United States Patent [19]

Sanders et al.

[11] Patent Number: 4,870,206
[45] Date of Patent: Sep. 26, 1989

[54] AROMATIC POLYISOCYANATES, THEIR PREPARATION AND USE AS COMPONENTS FOR ADHESIVES

[75] Inventors: Josef Sanders, Cologne; Rudolf Hombach; Helmut Reiff; Dieter Dieterich, all of Leverkusen; Manfred Dollhausen, Odenthal, all of Fed. Rep. of Germany

[73] Assignee: Bayer Aktiengesellschaft, Bayerwerk, Fed. Rep. of Germany

[21] Appl. No.: 210,908

[22] Filed: Jun. 24, 1988

[30] Foreign Application Priority Data

Jul. 8, 1987 [DE] Fed. Rep. of Germany ....... 3722499

[51] Int. Cl.$^4$ .............................................. C07C 69/00
[52] U.S. Cl. ....................................... 560/359; 528/85
[58] Field of Search ......................................... 560/359

[56] References Cited

U.S. PATENT DOCUMENTS 4,597,910  7/1986  König et al. ......................... 560/359

FOREIGN PATENT DOCUMENTS 1126379  3/1962  Fed. Rep. of Germany .
1959462  6/1971  Fed. Rep. of Germany .

OTHER PUBLICATIONS

Kunststoff Handbuch, vol. 7, Polyurethane, 2nd Ed. 1983, p. 15.
Kunststoff Handbuch, vol. 7, Polyurethane, 1983, pp. 581–596.
Corresponding pages in English Version, pp. 548–562.

Primary Examiner—Alan Siegel
Attorney, Agent, or Firm—Gene Harsh; Joseph C. Gil; Aron Preis

[57] ABSTRACT

New compounds containing isocyanatophenoxy groups, corresponding to

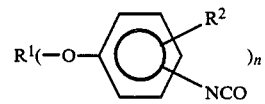

wherein $R^1$ denotes a residue of a n-valent polyhydroxyl compound having a molecular weight of about 92–6000, $R^2$ denotes hydrogen or methyl group and n denotes an integer of from 3 to 8 were found to be suitable as hardeners in the preparation of adhesives.

4 Claims, No Drawings

AROMATIC POLYISOCYANATES, THEIR PREPARATION AND USE AS COMPONENTS FOR ADHESIVES

FIELD OF THE INVENTION

This invention relates to new compounds containing three or more isocyanatophenoxy groups, to a process for their preparation and to their use as hardener component for the preparation of adhesives.

BACKGROUND OF THE INVENTION

Numerous aromatic polyisocyanates containing more than two isocyanate groups per molecule are known. It is also known that such polyisocyanates are potentially suitable as starting materials for the preparation of adhesives. Representatives of this class of compounds which have achieved a position of technical importance are described, for example, in Kunststoff Handbuch, Vol. 7: Polyurethane, published by G. Oertel, 2nd Edition, Hanser Verlag, Münich 1983, pages 13 to 15 and 581 to 596. The following are typical examples of such polyisocyanates: Tris-(4-isocyanatophenyl methane, polymer-diisocyanatodiphenylmethane, thiophosphoric acid tris-(p-isocyanatophenylester), the adduct of trimethylolpropane and 2,4-diisocyanatotoluen, etc. Thiophosphoric acid tris-(p-isocyanatophenyl)-ester is particularly distinguished by its good adhesive properties on various types of rubber as well as being virtually colorless and is therefore widely used as adhesive for sensitive, light colored materials.

Although the known polyisocyanates have reached a high level of quality in their adhesive properties, further improvements are desirable in view of the higher standards demanded, especially with regard to the heat resistance and compatibility with solvent-containing adhesives based on natural rubber and polychloroprene.

It is therefore an object of the present invention to provide new polyisocyanates which have such improved properties.

SUMMARY OF THE INVENTION

The present invention relates to novel compounds containing isocyanatophenoxy groups, corresponding to

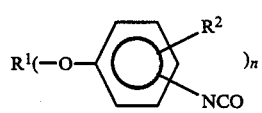

wherein
R¹ denotes a residue of a n-valent polyhydroxyl compound having a molecular weight of about 92–6,000,
R² denotes hydrogen or methyl group and
n denotes an integer of 3 or more which compounds were found to be suitable as hardeners in the preparation of adhesives.

DETAILED DESCRIPTION OF THE INVENTION

This invention relates to new aromatic polyisocyanates corresponding to the general formula (I):

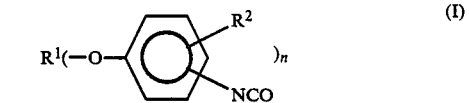

wherein
R¹ denotes a n-valent residue obtained by removal of the hydroxyl groups from a n-valent polyhydroxyl compound in the molecular weight range of from 92 to 6000, preferably from 92 to 400,
R² is hydrogen or a methyl group preferably hydrogen, and
n denotes an integer of 3 or more, preferably from 3 to 8, most preferably from 3 to 6.

The compounds have excellent adhesive properties combined with good color qualities and are superior, to the above-mentioned thiophosphoric acid tris-(p-isocyanatophenyl) esters in terms of the heat resistance of the bonds obtained and in promoting bonding and compatibility with solvent-containing adhesives based on natural rubber and polychloroprene.

This invention also relates to a process for the preparation of compounds of formula (I) above by a process comprising
(a) reacting a polyhydroxyl compound corresponding to formula (II)

$$R^1(OH)_n \quad (II)$$

with compounds corresponding to formula (III)

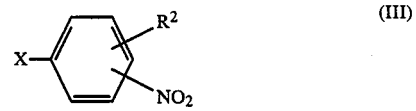

wherein
R¹, R² and n have the meaning indicated above and
X denotes a halogen, e.g. fluorine, preferably chlorine, and in which the halogen atom and the nitro group are preferably in the ortho- or para-position to one another,
in the presence of alkaline compounds to form the corresponding nitrophenoxy adducts corresponding to formula (IV):

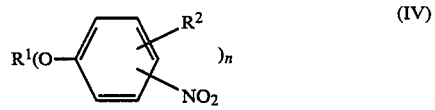

and
(b) hydrogenating the nitrophenoxy adducts in a known manner to form the corresponding aminophenoxy adducts and (c) converting the aminophenoxy adducts to the compounds of formula (I) by a known reaction, preferably by phosgenation.

Lastly, the invention relates to the use of the novel isocyanates, in particular as hardener components for the preparation of adhesives.

Suitable polyvalent hydroxyl compounds of formula (II) include, dinuclear or multinuclear phenols having a valence of 3 or more, preferably araliphatic, and most preferably aliphatic alcohols containing 3 or more hydroxyl groups. The polyvalent hydroxyl compounds of formula (II) may be, for example, condensation products of formaldehyde and phenol, hydroquinone, pyrocatechol or resorcinol; or pyrogallol, phloroglucinol, 1,2,4-trihydroxybenzene or, preferably, D(−)-sorbitol, D(−)-mannitol, (±)1,2,6-hexanetriol, hexanetriol (commercial isomeric mixtures), the series from 1,1,1-trimethylolethane to 1,1,1-trimethyloloctadecane, glycerol, dipentaerythritol and, most preferably, 1,1,1-trimethylolpropane and pentaerythritol. The alcoholic starting materials may also be products of addition of epoxides such as ethylene oxide, propylene oxide, butylene oxide, styrene oxide, epichlorohydrin or higher membered cyclic ethers such as tetrahydrofuran or tetrahydropyran to the above mentioned polyhydroxyl compounds, which products of addition may be prepared with the aid of acid catalysis, e.g. in the presence of $BF_3$. or basic catalysis, by known processes. These epoxides may be added to the above-mentioned polyhydroxyl compounds either in their pure form or as mixtures or successively. It is also advantageous to use partially esterified polyvalent polyhydroxyl compounds, e.g. pentaerythritol mono-fatty acid esters. It may in some cases be advantageous to use mixtures of the above mentioned polyhydroxyl compounds.

The following are examples of preferred compounds within the scope of formula (III)' 2-Nitrochlorobenzene, 2-nitrofluorobenzene, 4-nitrochlorobenzene, 4-nitrofluorobenzene, 1-methyl-2-nitro-3-chlorobenzene, 1-methyl-2-nitro-3-fluorobenzene, 1-methyl-4-nitro-5-chlorobenzene, 1-methyl-4-nitro-5-fluorobenzene, 1-methyl-2-nitro-6-chlorobenzene and 1-methyl-2-nitro-6-fluorobenzene. 2-Nitrochlorobenzene and 4-nitrochlorobenzene are particularly preferred starting materials within the scope of formula (III).

The alkaline compounds used for the reaction of the polyhydroxyl compounds (II) with the halogenated nitrobenzene (III) may be, for example, metal hydrides or metal alkoxides or, preferably, metal hydroxides. Sodium hydroxide and potassium hydroxide are particularly preferred.

For carrying out stage a) of the process according to the invention, the starting materials (III) may be used either in the stoichiometric quantity or in an excess or subequivalent quantity, based on the quantity of component (II). Component (III) is preferably used in the quantity of from 1 to 1.5 mol of component (III) for each mol of hydroxyl groups in component (II).

The hydrogen halide released in the reaction is bound by the addition of metal hydrides, metal oxides or metal hydroxides, as already mentioned. These are used in sufficient quantity for neutralization of the hydrogen chloride released. They are preferably used in a quantity providing from 1 to 3 mol equivalents of base per mol of hydroxyl groups.

Stage (a) of the process may be carried out in the absence of solvent but is advantageously carried out in an organic solvent, optionally in the presence of a phase transfer catalyst. The reactants may be present in a homogeneous phase or in two phases, dissolved, emulsified or suspended.

The following are examples of suitable organic solvents: Benzene, toluene, xylene, chlorobenzene, dichlorobenzene, trichlorobenzene, diethylether, diisopropylether, tert.-butyl methyl ether, tetrahydrofuran, dioxane, ethylene glycol dimethylether, ethyl acetate, acetone, methyl ethyl ketone, acetonitrile, furfurol, methylene chloride, chloroform, trichloroethylene, tetrachloroethylene, nitromethane or nitropropane.

Polar aprotic solvents such as dimethylformamide, dimethylacetamide, N-methylpyrrolidone, tetramethylurea, N-methylcaprolactam, dimethylsulphoxide, tetramethylenesulphone, hexamethylene phosphoric acid triamide, etc. are preferred. Dimethylformamide, dimethylsulphoxide and N-methylpyrrolidone are particularly preferred. Any mixtures of such solvents may, of course, also be used.

The quantity of solvent is generally calculated to be sufficient to form clear solutions of the starting materials (II) and (III). In practice, this means that the solvents are generally used in a quantity of from 50 to 1000 parts by weight, preferably from 100 to 500 parts by weight of solvent per 100 parts by weight of the mixture of components (II) and (III).

It may in some cases be advantageous to carry out the reaction in the presence of a phase transfer catalyst. Such catalysts are described, for example, in E. V. and S. S. Dehmlow, Phase Transfer Catalysis, 2nd Edition, Verlag Chemie 1983. Quaternary ammonium and phosphonium salts corresponding to the following formula are among the suitable catalysts:

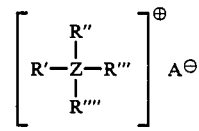

In the above formula,

Z stands for nitrogen or phosphorus and

R', R'', R''' and R'''' denote identical or different alkyl groups with 1 to 18 carbon atoms but one of these groups may be an araliphatic group with 7 to 15 carbon atoms'. and the sum of carbon atoms of the four groups is preferably from 12 to 31.

The following are typical examples of suitable catalysts: N-Benzyl-N,N,N-triethylammonium chloride or bromide, N-benzyl-N-dodecyl-N,N-dimethylammonium chloride or bromide, N-benzyl-N,N-tri-n-octyl ammonium chloride or bromide and the phosphonium salts corresponding to these ammonium salts.

In the process, the quaternary ammonium and phosphonium salts mentioned above as examples are preferably added solvent-free or in the form of their aqueous solutions (for example with a solids content of from 30 to 60% weight) and preferably in a quantity of from 1 to 10 mol-%, based on the molar quantity of the hydroxyl groups present. When the preferred polar aprotic solvents according to the invention are used, e.g. dimethylformamide, N-methylpyrrolidone or dimethylsulphoxide, there is no disadvantage in dispensing with the addition of phase transfer catalysts.

Stage (a) of the process is generally carried out at 10° to 100° C., preferably at 20° to 60° C., at excess pressure or reduced pressure or preferably without pressure, either continuously or discontinuously. The residence time is generally from 0.5 to 24 hours, preferably from 0.5 to 8 hours. Stage (a) may be carried out, for example, by introducing the starting materials and optionally the phase transfer catalyst in the selected solvent into the reaction vessel and then continuously adding the base in the form of a solution or suspension, preferably in a solid, very finely ground form, with stirring, either in increments or continuously and optionally with cooling. Stirring is then continued at room temperature or optionally elevated temperature until the IR spectrum indicates complete conversion of the hydroxyl groups originally present and/or until no starting material (III) can be detected by thin layer or gas chromatography. Working up of the nitrophenoxy compound is carried out in known manner. The nitrophenoxy compounds are in many cases difficult to dissolve in the solvents used so that the major proportion thereof precipitates when the reaction mixture is cooled to room temperature and can therefore be isolated by simple filtration. Another method of working up entails stirring the reaction mixture into water and isolating the precipitated reaction product by filtration in the usual manner. If the reaction products are oily, however, it is advisable to work them up by extraction by known usual methods, in which case the extracting agent used for the reaction mixture which is mixed with water may be, for example, toluene, methylene chloride, chlorobenzene, dichlorobenze, 1,2-dichloroethane, trichloroethane, among others.

The reaction mixture obtained in stage (a) may also be directly transferred to stage (b) without an intermediate stage of isolation, optionally after neutralization of the excess alkali metal hydroxide.

The compounds obtained in stage (a) of the invention, which contain nitrophenoxy end groups, are converted into the corresponding polyamines in stage (b) by reduction in a known manner, using nascent hydrogen or hydrogen which is catalytically activated, for example with Raney nickel or palladium on charcoal. Hydrogenation may be carried out in the presence or absence of inert solvents at 20° to 120° C. and under a pressure of 20 to 80 bar. Methanol, ethanol, i-propanol, toluene, DMF, etc. for example are suitable solvents, DMF and methanol are preferred. The resulting polyamines are obtained as distillation residues from the distillative removal of solvent and may in most cases be further processed without additional purification steps but optionally after washing with a suitable organic solvent.

The polyamines obtained in stage (b) are then converted into the corresponding polyisocyanates by reaction with phosgene in stage (c). Both the free amines and their addition products with hydrogen chloride or carbon dioxide may be used for this reaction. The phosgenation is generally carried out in chlorobenzene or dichlorobenzene, a reaction medium which is generally a dispersing agent or solvent for the free amines, depending on their constitution, and a solvent for the isocyanates. Phosgenation is in other respects carried out by known methods, for example as described in DE-A-No. 3,442,689, in Liebigs Annalen der Chemie, Volume 562, Year 1949, pages 75 to 109 in Ullmanns Encyclopädie der technischen Chemie, Volume 14, 4th Edition, 1977, pages 350 to 354 or in Houben-Weyl, Methoden der organischen Chemie, Volume E 4, 4th Edition, 1983, pages 741 to 753.

The isocyanates of the invention may also be prepared by phosgene-free processes as described, for example, in the last mentioned literature reference on page 761 et seq. Amines, for example, may be converted into isocyanates by a reaction with nickel carbonyl or carbon monoxide in the presence of noble metal catalysts. Nitro compounds, for example, may be converted into isocyanates with carbon monoxide in the presence of noble metals or noble metal complex compounds.

The trifunctional or higher functional aromatic isocyanates obtained from working up the reaction mixture are generally viscous oils or low melting solids and are distinguished by excellent adherence to materials such as rubber, metals, glass, etc. and their comparative lack of self color. They are therefore particularly suitable for the preparation of adhesives, as already mentioned above. For this purpose, the novel polyisocyanates are reacted with the known reactants used for this purpose. Suitable starting components for the preparation of adhesives are mentioned, for example, in Kunststoff Handbuch, Vol. 7: Polyurethane, published by C. Oertel, 2nd Edition, Hanser Verlag, Munich 1983, pages 581 to 596, or in Ullmanns Encyclopädie der technischen Chemie, Vol. 14, 4th Edition, Verlag Chemie, Weinheim 1977, pages 227 to 268. These publications also mention auxiliary agents and additives optionally used for the preparation and application of the adhesives.

For the preparations of adhesives, the novel polyisocyanates of the invention are combined with binders commonly used for this purpose. The following are examples of such binders:

1. The natural types of rubbers conventionally used as adhesives or adhesive raw materials;

2. The synthetic rubber types conventionally used as adhesives or adhesive raw materials, e.g. polymers of dienes such as butadiene or copolymers of dienes such as butadiene with simple olefinically unsaturated compounds such as styrene, acrylonitrile or methacrylonitrile, and polymers or copolymers of 2-chloro-butadiene-(1,3) with other olefinically unsaturated monomers, for example of the type mentioned above, in particular with a chlorine content of about 36% by weight, or 3. The hydroxyl-containing polyurethanes conventionally used as adhesives or adhesive raw materials, generally with molecular weights (determined by gel chromatography) of 30,000 to 1,000,000, preferably from 50,000 to 200,000, in particular straight chained or substantially straight chained polyurethanes carrying hydroxyl end groups, obtained from (i) dihydroxypolyesters in the arithmetically calculated molecular weight range of from 1250 to 4000, preferably from 2000 to 4000, obtained from aliphatic or aromatic dicarboxylic acids such as adipic acid or phthalic acid and alkanediols such as ethylene glycol, tetramethylene glycol and/or hexamethylene glycol or from polylactones, in particular poly-$\epsilon$-caprolactone, and (ii) aromatic or aliphatic diisocyanates, in particular 2,4-diisocyanatotoluene and mixtures thereof with 2,6-diisocyanatotoluene, 4,4-diisocyanatodiphenylmethane or hexamethylenediisocyanate, optionally with the addition of (iii) glycols in the molecular weight range of from 62 to 200 as chain lengthening agents, e.g. tetramethylene glycol or hexamethylene glycol, in a molar NCO/OH equivalent ratio of from 0.9:1 to 0.999:1.

The particularly preferred adhesive agents include the polymers and copolymers of 2-chlorobutadiene-(1,3) (polychloroprene) exemplified above and the last mentioned polyurethanes which contain hydroxyl groups.

The above-mentioned binders and adhesive raw materials are preferably used as 10 to 30% by weight solutions in solvents or solvent mixtures of the type already mentioned above as examples.

The polyisocyanate mixtures are added to these solutions in quantities of from 2 to 15% by weight, based on the above-mentioned binders. For rapid and homogeneous mixing of the solution of adhesive with the polyisocyanate it is frequently advantageous to add the polyisocyanate mixtures as 10 to 50% by weight solutions in such solvents to the binder solutions.

The adhesives may also be mixed with other additives to modify their adhesive technical properties. These additives include, for example, natural resins or modified resins such as colophony esters or synthetic resins such as phthalic resins or, especially in the case of adhesives based on polyurethanes containing hydroxyl groups, they may also consist of polymers such as chlorine rubber or soluble polymers or copolymers of vinyl acetate or other vinyl compounds. These additives, in particular the resins mentioned as examples, are generally added for the purpose of obtaining exceptionally long lasting contact bonding or for increasing the cohesive strength.

The adhesive solutions containing the polyisocyanate mixtures are suitable for bonding any materials to similar or different materials, e.g. for bonding leather, textiles, plastics, wood or paper, preferably for bonding rubber or soft PVC.

In addition, the polyisocyanates may be used or added as one of the components for the preparation of polyurethanes or polyurethane ureas as well as for any other known reactions of isocyanates, such as carbodiimidization, uretdionization, isocyanurate formation, amide formation, etc.

It should also be noted that the polyamines obtained as intermediate products in stage (b) of the process are not only suitable as starting materials for the diisocyanates but are also excellent cross-linking agents or chain lengthening agents for precursors of plastics, for example for isocyanate prepolymers used for the preparation of polyurethane elastomers or for epoxide resins. The polyamines may be used for these purposes instead of the polyamines hitherto used for such applications.

The invention is further illustrated but is not intended to be limited by the following examples in which all parts and percentages are by weight unless otherwise specified. The average particle size of the pulverulent sodium hydroxide used is from 6 to 9 μm.

EXAMPLES

EXAMPLE 1

(a) Nitrophenylation 180 g (4.5 mol) of powdered sodium hydroxide is added in small portions to a solution of 92 g of glycerol (1 mol) and 519.8 g (3.3 mol) of 4-nitrochlorobenzene in 1 liter of dimethylsulphoxide (DMSO) at 50° C. with vigorous stirring over a period of 2 hours and stirring is then continued at this temperature for a further 4 hours. After cooling to room temperature, the precipitated product is suction filtered, washed neutral with water, washed again with ethyl acetate and then dried in a vacuum at 100° C.

Yield: 319 g (70% of the theory).
Mp.: 208° to 209° C. (slightly yellowish powder).

(b) Hydrogenation 1215 g (2.67 mol) of the nitrophenoxy adduct according to Example (1a) are hydrogenated in 5 liter of methanol in the presence of 125 g of Raney nickel at 70° C. and 50 bar. When uptake of hydrogen has been completed, the catalyst is removed by filtration and the solvent is drawn off under vacuum.

Yield: 955 g (98% of the theory).
Dark oil (GC: 96%).

(c) Phosgenation

About 300 g of phosgene are rapidly added with stirring at −10° C. to an emulsion of 156 g (0.41 mol) of the aminophenoxy adduct of Example (1b) in 2.2 liter of chlorobenzene. The mixture is then heated to reflux with slow introduction of phosgene (40–50 g/h) in the course of 5 hours and then boiled under reflux for a further hour, an almost clear solution was obtained. Excess phosgene is blown out with nitrogen and the undissolved material is filtered off. After the solvent has been drawn off, a brownish, viscous crude product is obtained which can be almost completely decolorized by treatment with neutral silica gel of grain size 0.063 to 0.2 mm.

Yield: 151 g (83% of the theory) (light yellow, viscous oil).
NCO content: Calc.: 28.4%, Found: 27.8%.

EXAMPLE 2

(a) Nitrophenylation 180 g (4.5 mol) of powdered sodium hydroxide is added in small portions to a solution of 120 g (1 mol) of 1,1,1-trimethylolethane and 519.8 g (3.3 mol) of 4-nitrochlorobenzene in 1.4 liter of dimethylsulphoxide over a period of 2 hours with stirring while the reaction temperature is maintained at 40°–50° C. by cooling with water. Stirring is continued for a further 4 hours at room temperature after all the sodium hydroxide has been added and the product is then worked up as in Example (1a).

Yield: 397 g (82% of the theory).
Mp.: 189 to 191° C. (almost colorless powder).

(b) Hydrogenation 380 g (0.79 mol) of the nitrophenoxy adduct of Example (2a) are hydrogenated in 1.6 liter of methanol in the presence of 40 g of Raney nickel by a method analogous to that of Example (1b).

Yield: 263 g (85% of the theory).
Mp.: 137° to 139° C. (almost colorless powder).

(c) Phosgenation

About 300 g of phosgene are rapidly added with stirring at −10° C. to a suspension of 150 g (0.38 mol) of the aminophenoxy adduct of Example (2b) in 2.2 liter of chlorobenzene. Phosgenation is then carried out to completion as described in Example (1c).

Yield: 156 g (87% of the theory) (pale yellow, viscous oil).
NCO content: Calc.: 26.8%, Found: 26.2%.

EXAMPLE 3

(a) Nitrophenylation 134 g (1 mol) of 1,1,1-Trimethylolpropane, 519.8 g (3.3 mol) of 4-nitrochlorobenzene and 180 g (4.5 mol) of powdered sodium hydroxide are reacted together in 1.4 liter of DMSO as in Example (1a).

Yield: 457 g (92% of the theory).
Mp.: 172° to 174° C. (almost colorless powder).

When the analogous reaction is carried out in 1.5 liter of dimethylformamide (DMF) instead of DMSO as solvent, the yield obtained is 393 g (79% of the theory).

(b) Hydrogenation 400 g (0.8 mol) of the nitrophenoxy adduct from Example (3a) are hydrogenated in 1.6 liter of methanol in the presence of 45 g of Raney nickel by a reaction analogous to that of Example (1b). The crude product obtained is washed with cold toluene.

Yield: 306 g (94% of the theory).
Mp.: 117° to 118° C. (pale grey powder).

(c) Phosgenation 150 g (0.37 mol) of aminophenoxy adduct from Example (3b) are phosgenated in 2.2 liter of chlorobenzene by a reaction analogous to that of Example (2c).

Yield: 160 g (89% of the theory) (pale yellow, viscous oil).

NCO content: Calc.: 26%, Found: 25.3%.

EXAMPLE 4

(a) Nitrophenylation 136 g (1 mol) of pentaerythritol, 693 g (4.4 mol) of 4-nitrochlorobenzene and 240 g (6 mol) of powdered sodium hydroxide are reacted in 1.8 liter of DMSO by a method analogous to that of Example (2a).

Yield: 595 g (96% of the theory).
Mp.: 285° to 286° C. (pale yellow powder).

When the analogous reaction is carried out in 2 liter of N-methylpyrrolidone in DMSO as solvent, the yield obtained is 521 g (84% of the theory).

(b) Hydrogenation 400 g (0.65 mol) of the nitrophenoxy adduct from Example (4a) are hydrogenated in 1.8 liter of DMF in the presence of 60 g of Raney nickel by a method analogous to that of Example (1b). The crude product is washed with cold toluene.

Yield: 299 g (92% of the theory).
Mp.: 210° to 211° C. (pale grey powder).

(c) Phosgenation 150 g (0.3 mol) of the aminophenoxy adduct according to Example (4b) are phosgenated in 2.2 liter of chlorobenzene by a method analogous to that of Example (2c).

Yield: 174 g (96% of the theory) (pale yellow, viscous oil).

NCO content: Calc.: 27.8%, Found: 27.3%.

EXAMPLE 5

(a) Nitrophenylation 136 g (1 mol) of pentaerythritol, 693 g (4.4 mol) of 2-nitrochlorobenzene and 240 g (6 mol) of powdered sodium hydroxide are reacted together in 2.3 liter of DMSO by a method analogous to that of Example (2a).

Yield: 492 g (79% of the theory).
Mp.: 214° to 217° C. (almost colorless powder).

(b) Hydrogenation 480 g (0.77 ml) of the nitrophenoxy adduct according to Example (5a) are hydrogenated in 1.6 liter of DMF in the presence of 50 g of Raney nickel by a method analogous to that of Example (1b).

Yield: 348 g (90% of the theory).
Mp.: 138° to 139° C. (almost colorless powder).

(c) Phosgenation 150 g (0.3 mol) of the aminophenoxy adduct according to Example (5b) are phosgenated in 2.2 liter of chlorobenzene by a method analogous to that of Example (2c).

Yield: 158 g (87% of the theory).
Mp: 177°-178° C. (colorless crystals).
NCO content: Calc.: 27.8%, Found 27,4 %.

EXAMPLE 6

(a) Nitrophenylation 134 g (1 mol) of (±)-1,2,6-Hexanetriol, 519.8 g (3.3 mol) of 4-nitrochlorobenzene and 180 g (4.5 mol) of powdered sodium hydroxide are reacted together in 2.2 liter of DMSO by a method analogous to that of Example (2a).

Yield: 352 g (71% of the theory).
Mp.: 115° to 116° C. (yellowish powder).

(b) Hydrogenation 400 g (0.8 mol) of the nitrophenoxy adduct according to Example (6a) are hydrogenated in 1.6 liter of methanol in the presence of 50 g of Raney nickel by a method analogous to that of Example (1b).

Yield: 290 g (89% of the theory).
Dark, viscous oil.

(c) Phosgenation 150 g (0.37 mol) of the aminophenoxy adduct according to Example (6b) are phosgenated in 2.2 liter of chlorobenzene by a method analogous to that of Example (1c).

Yield: 154 g (86%) (pale brown, viscous oil).
NCO content: Calc.: 26%, Found 25.4%.

EXAMPLE OF PRACTICAL APPLICATION

Polyurethane adhesives were prepared as follows:

A substantially straight chained polyurethane containing hydroxyl groups and having a molecular weight, (determined by gel chromatography) of about 100,000 was prepared from 2,4-toluylene diisocyanate and a hydroxyl-containing polyester of adipic acid, and ethylene glycol and was dissolved in methyl ethyl ketone to form an approximately 20% solution having a viscosity of 2 Pa.s at 20° C. 100 Parts of this polyurethane solution were thoroughly mixed with 5 parts of one of the polyisocyanate solutions described below.

The polyisocyanates of Examples (3c) and (4c) were dissolved in ethyl acetate to form a solution having an isocyanate content of 5.4%. As comparison example there was used an approximately 20% solution of thiophosphoric acid-tris-(p-isocyanato)-phenyl ester in methylene chloride having an isocyanate content of 5.4%, which has been disclosed, for example, in DE-PS No. 1,126,379, Example (2. The adhesives which were thus prepared are identified below as Example (3c), Example (4c), and Comparison Example (.

Test Materials

The adhesives are tested according to DIN 53,273 on the test materials described below.

Test Material A: Styrene-butadiene rubber shoe sole material with Shore A hardness 90.

Test Material B: PVC containing 30% of dioctylphthalate as plasticizer.

Adhesive bonds

Test samples were prepared from the test materials according to DIN 53,273 to test the adhesives. Before applying the adhesive, the rubber material was thoroughly rubbed down with a grain 40 abrasive paper. The adhesive was applied twice on each side so that each side carried about 50 g/m² of adhesive, based on the solids content.

After 30 seconds for evaporation, the film of adhesive on one side was heated to a temperature of about 80° C.

by radiant heat (4 seconds on an apparatus of Funck AG, Munich) and the adhesive surfaces were placed together and then put under a pressure of 0.4 MPa for 10 seconds. After the samples have been glued, they were stored at 20° C. for 9 days. The resistance to peeling determined by a separation test according to DIN 53 273 at a spindle feed rate of 100 mm/min at 23° C.. is entered in the following Table:

| Test Material | Peeling resistance N/mm | | Comparison Example |
|---|---|---|---|
| | Example 3c | Example 4c | |
| A | 9.6 | 10.6 | 7.5 |
| B | 7.1 | 8.3 | 6.8 |

The bonds obtained with the isocyanates according to the invention are found to have greater strength than those of the Comparison example. Heat resistance of fresh bonds:

The heat resistance of fresh bonds was determined by the peeling test immediately after their formation. For this test, bonds on test material A were stored at 50° C. for one hour immediately after their formation. The resistance to peeling was determined immediately on the test sample which was still at a temperature of 50° C.

| Adhesive | Resistance to peeling N/mm |
|---|---|
| Example 3c | 4.6 |
| Example 4c | 6.8 |
| Comparison Example | 7.1 |

Compared with the Comparison example, the bonds obtained with the isocyanates according to the invention have lower initial strength values. This is an advantage for many purposes of application as it allows a longer time interval for any corrections required.

Heat resistances of adhesive bonds which had been kept in storage

After a ventilation time of 30 minutes, the adhesive surfaces were heated to a temperature of from 80° to 85° C. by radiant heat within 4 seconds. The adhesive strips were placed together to form an overlapping area of 2.5×2.5 cm and the samples were put under a pressure of 4 MPa for 10 seconds.

To determine t heat resistance according to ASTM 816 D, the test samples, each of which had been stored at room temperature for 9 days, were subjected to a shearing test. In this test, the samples are put under a load of 11 kg. after 20 minutes' tempering at 40° C., the temperature at which the bond fails is determined by raising the temperature by 0.25 degrees Centigrade per minute. The temperature reached are shown in the following Table.

| Adhesive | Temperature °C. |
|---|---|
| Example 3c | 102 |
| Example 4c | 109 |
| Comparison Example | 91 |

The bonds containing the isocyanates according to the invention show higher values for heat resistance than the Comparison example.

Although the invention has been described in detail in the foregoing #or the purpose of illustration, it is to be understood that such detail is solely for that purpose and that variations can be made therein by those skilled in the art without departing from the spirit and scope of the invention except as it may be limited by the claims.

What is claimed is:

1. A compound containing isocyanatophenoxy groups having the formula:

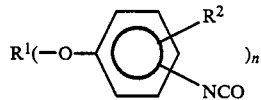

wherein
$R^1$ denotes the residue obtained by removal of the hydroxyl groups from a n-valent polyhydroxyl compound having a molecular weight of about 92 to 6000,
$R^2$ denotes a methyl radical or hydrogen and
n denotes an integer from 3 to 8.

2. The compound of claim 1, wherein said molecular weight is about 92 to 400 and said n denotes an integer from 3 to 6.

3. The compound of claim 1 wherein said $R^1$ denotes an aliphatic hydrocarbon radical.

4. The compound of claim 1 wherein said $R^2$ denotes hydrogen and wherein the group $R^1O$ and the isocyanate group are in the ortho- or para-position to one another.

* * * * *